United States Patent
Aitken et al.

(10) Patent No.: US 8,123,924 B2
(45) Date of Patent: Feb. 28, 2012

(54) SPERM CELL SEPARATION BY ELECTROPHORESIS

(75) Inventors: Robert J. Aitken, Cooks Hill (AU); Christopher J. Ainsworth, Newcastle (AU)

(73) Assignee: Newcastle Innovation Limited, Callaghan (AU)

( * ) Notice: Subject to any disclaimer, the term of this patent is extended or adjusted under 35 U.S.C. 154(b) by 847 days.

(21) Appl. No.: 10/574,911

(22) PCT Filed: Oct. 7, 2004

(86) PCT No.: PCT/AU2004/001367
§ 371 (c)(1),
(2), (4) Date: May 11, 2007

(87) PCT Pub. No.: WO2005/033295
PCT Pub. Date: Apr. 14, 2005

(65) Prior Publication Data
US 2009/0101507 A1    Apr. 23, 2009

(30) Foreign Application Priority Data
Oct. 7, 2003 (AU) ................................ 2003905474

(51) Int. Cl.
G01N 27/447 (2006.01)
A61B 17/43 (2006.01)
B01D 61/42 (2006.01)

(52) U.S. Cl. ............................ 204/456; 600/35; 204/543

(58) Field of Classification Search .................. 204/450, 204/600, 400, 403.01, 403.06, 403.07, 792, 204/793, 540, 456, 543; 600/35
See application file for complete search history.

(56) References Cited

U.S. PATENT DOCUMENTS

| | | | |
|---|---|---|---|
| 4,055,799 A | 10/1977 | Coster et al. | |
| 4,323,439 A | 4/1982 | O'Farrell | |
| 5,071,536 A | 12/1991 | Ivory | |
| 5,336,387 A | 8/1994 | Egen et al. | |
| 5,427,946 A * | 6/1995 | Kricka et al. | 435/288.5 |
| 5,906,724 A | 5/1999 | Sammons et al. | |
| 6,001,617 A * | 12/1999 | Raptis | 435/173.1 |
| 6,491,819 B2 | 12/2002 | Prince et al. | |
| 6,638,408 B1 * | 10/2003 | Speicher et al. | 204/458 |
| 6,824,995 B1 | 11/2004 | Wu | |
| 7,070,917 B1 * | 7/2006 | Christensen et al. | 435/2 |
| 7,214,299 B2 | 5/2007 | Armstrong | |
| 2002/0043465 A1 | 4/2002 | Vigh et al. | |
| 2002/0119218 A1 * | 8/2002 | Burke et al. | 426/24 |
| 2003/0029725 A1 | 2/2003 | Conlan et al. | |

(Continued)

FOREIGN PATENT DOCUMENTS

CN            89105110.4         *    1/1991

(Continued)

OTHER PUBLICATIONS

Engelmann, Ute et al. "Separation of Human X and Y Spermatozoa by Free-Flow Electrophoresis." Gamete Research 19:151-159 (1988).*

(Continued)

Primary Examiner — Alex Noguerola
(74) Attorney, Agent, or Firm — McKeon, Meunier, Carlin & Curfman, LLC (57) ABSTRACT

A process for separating a sperm type from a sperm population by electrophoresis comprising subjecting the sperm population to an electric potential such that a sperm type is separated from a sperm population through an ion-permeable barrier.

29 Claims, 7 Drawing Sheets

U.S. PATENT DOCUMENTS

2008/0067070 A1 3/2008 Rylatt et al.

FOREIGN PATENT DOCUMENTS

| DE | 101 49 875 | A1 | | 7/2003 |
|---|---|---|---|---|
| WO | WO 02/24134 | A1 | | 3/2002 |
| WO | WO 02/093168 | A1 | | 11/2002 |
| WO | WO 2004/101117 | A1 | * | 10/2004 |

OTHER PUBLICATIONS

English language translation of CN 89105110.4 patent published on Jan. 2, 1991.*

Moore et al. "Isoelectric Focusing of Boar Spermatozoa," J. Reprod. Fert. (1975) 44, 329-332.*

Moore "The Net Surface Charge of Mammalian Spermatozoa as Determined by Isoelectric Focusing, Changes Following Sperm Maturation, Ejaculation, Incubation in the Female Tract, and after Enzyme Treatment" International Journal of Andrology 2 (1979) 449-452.*

"Genes and Chromosomes" article produced by the Centre for Genetics Education downloaded from www.genetics.edu.au on Jun. 5, 2010.*

Jaspers et al. "Separation of Bacterial Cells by Isoelectric Focusing, a New Method for Analysis of Complex Microbial Communities," Applied and Environmental Microbiology, Aug. 1997., p. 3176-3181.*

Master's Thesis by Breanna Tilley entitled "Assessment of Boar Sperm Samples by Computer-Assisted Sperm Analysis and the Mobilty Assay," Texas Tech University, May 2007.*

McHenry, J.., "International Search Report," PCT/AU2004/001367, 3 pages, Australian Patent Office, Australia (mailed Nov. 19, 2004).

Klemm, M., "Device for extracting electrically charged molecules, useful e.g. in environmental monitoring or clinical diagnosis, comprises electrodes, containers and a matrix permeable to analyte," Derwent World Patents Index, Dialog File 351, Accession No. 15508313, 2 pages, Derwent Information Ltd. (2003).

* cited by examiner

SPERM CELL SEPARATION BY ELECTROPHORESIS

This application is a 371 of PCT/AU2004/001367, filed Oct. 7, 2004, which claims priority to Australian Patent Application 2003905474, filed Oct. 7, 2003, which is herein incorporated by reference in its entirety for all purposes.

TECHNICAL FIELD

The present invention relates to the use of membrane-based electrophoresis technology for isolating/enriching sperm population(s) from semen.

BACKGROUND ART

Most cell separation methods provide enrichment of a cell population rather than true purification. Methods that provide pure cell preparations are often slow and have low recovery. A number of cell isolation/separation techniques have been employed previously for purifying/enriching or removing a cell population(s) from a suspension and can be divided into three categories (Kumar and Lykke, 1984, Cell separation: a review, *Pathology*. January; 16(1):53-62). First, methods that exploit physical differences between cell populations (cell density, cell size, cell charge, optical properties) such as isopycnic density gradient centrifugation, velocity sedimentation, electrophoresis, phase partitioning, and flow cytometry. Second, methods in which separation is based upon differences in properties of the cell surface (adhesion, and surface antigen such as affinity and magnetic methods). Third, methods that separate cells on the basis of their functional characteristics such as proliferation, phagocytosis, and antigen recognition.

Paradoxically, although the purpose is mainly to separate functionally different cell populations, there are very few existing methods that are actually based upon differences in cell function. Techniques based upon cell surface properties have a good correlation with functional differences between cell populations. In recent years, those methods have been more widely used, especially in the area of stem cell purification. A disadvantage with using affinity methods, for example, is that they can often be expensive or time-consuming to perform and can cause considerable damage to, or activation of, desired cells and/or can add undesirable agents to the purified or isolated cell suspensions (e.g toxins, proliferation-inducing agents, and/or antibodies). An additional problem in the purification of stem cells using antibody-based methods is that the most primitive stem cells may not possess the antibody-targeted cell surface marker (e.g CD34) and such cells will not be recovered.

The most widely used techniques are those that rely on physical differences and electrophoresis falls into this category. The main form of electrophoresis used up to now is free-flow electrophoresis. This form involves laminar flow of cells through a specially designed chamber within an electric field. The different mobilities (different charge to mass ratios) of the cells in the electric field allows the cells to separate and they are collected through multiple channels at the end of the chamber. The extent to which these correlate with functional properties of the cells is variable.

Cell electrophoresis is a high resolution separation method. In traditional electrophoresis, sub-populations of cells for which no affinity ligand has been developed and for which there is no distinct size or density range are often separable on the basis of their electrophoretic mobility, which may be related to their function. The electrophoretic mobility of a cell is directly correlated with the cellular negative surface charge density.

The surface charge on cells will vary depending on the cell type, relative freshness of the cells, and the pH of the electrophoresis buffer used for separation. At physiological pH (around neutral), cells have a net negative surface charge and when placed in an electric field, they are deflected or moved towards the anode. In electrophoresis devices reported in the literature, fractionation is based on electrophoretic mobilities of the cells (Smolka, Margel et al. 1979, Electrophoretic cell separation by means of microspheres, *Biochim Biophys Acta*. 1979 Dec. 3; 588(2):246-55).

Some of the challenges faced by early investigators of electrophoretic cell separation were excessive heat generation, degree of resolution of the separated fractions and scalability of the technology.

At present there is no acceptable and practical means to separated or select sperm populations other than the time-consuming, inefficient process of density gradient centrifugation.

The present inventors provide a reliable, reproducible, rapid, efficient, and cost-effective method of enriching a sperm population from semen or other solutions using membrane-based electrophoresis technology.

DISCLOSURE OF INVENTION

In a first aspect, the present invention provides a process for separating a sperm type from a sperm population by electrophoresis comprising subjecting the sperm population to an electric potential such that a sperm type is separated from a sperm population through an ion-permeable barrier.

The sperm type can have a desired characteristic and that type is separated from the sperm population. Examples of a desired characteristics include, but not limited to, motility, robustness, gender, genetic make-up, morphological normality, fertilizing potential, and combination thereof. preferably, the sperm type has fertilizing potential.

The sperm type can have a undesired characteristic and that type is removed from the sperm population. An undesired characteristic would include poor motility, poor morphology, high levels of DNA damage and high levels of reactive oxygen species generation. Preferably leukocytes are also removed from the sperm preparations used for assisted conception, as these cells are potentially damaging to sperm.

Preferably, the process comprises:
(a) providing a sample containing sperm to a sample chamber of electrophoresis apparatus comprising a first electrolyte chamber; a second electrolyte chamber; a first sample chamber disposed between the first electrolyte chamber and the second electrolyte chamber; a second sample chamber disposed adjacent to the first sample chamber; a first ion-permeable barrier disposed between the first sample chamber and the second sample chamber; a second ion-permeable barrier disposed between the first electrolyte chamber and the first sample chamber; a third ion-permeable barrier disposed between the second sample chamber and the second electrolyte chamber; and electrodes disposed in the first and second electrolyte chambers; and
(b) applying an electric potential between the electrodes causing at least one sperm type in the first or second sample chamber to move through the first ion-permeable barrier into the other of the first or second sample chamber.

The sperm sample preferably contains at least two populations of sperm.

The electric potential can be applied until at least one sperm type reaches a desired purity.

Preferably, one or more ion-permeable barriers are electrophoresis membranes having a characteristic average pore size and pore size distribution.

In one form, all of the ion-permeable barriers are membranes have a characteristic average pore size and pore size distribution.

Preferably, the first ion-permeable barrier is a large pore sized membrane. Examples of suitable large pore sized membranes include, but are not limited to polycarbonate or polyacrylamide.

Typically a large pore size membrane has a pore size of about 1 to about 10 µm.

Preferably, the membrane has a pore size of about 5 µm.

Preferably, electrophoresis is carried out with a voltage range from about 1 to 200 V.

Electrophoresis can be carried out with an applied current of up to about 75 mA.

Electrophoresis can be carried out with a field strength of 1 to 100 V/cm. The present inventors have found that a field strength from about 16 to 20 V/cm is particularly suitable.

Electrophoresis is carried out from several seconds to about 15 minutes in an apparatus having a sample volume of about 100 µl to about 4 ml.

For processing, the sperm can diluted in buffer having a concentration of between about 1 to 100 mM.

Sperm concentrations of between about 0.1 and $250 \times 10^6$/ml can be readily processed. Sperm concentrations of between $15 \times 10^6$/ml and $140 \times 10^6$/ml have been processed successfully.

In another preferred form the step of applying an electric potential between the electrodes is maintained until at least one sperm type reaches a desired purity level in the first or second sample chamber.

At least some of the electrophoresis separation membranes are preferably made from polyacrylamide and have a molecular mass cut-off of at least about 5 kDa. The molecular mass cut-off of the membrane will depend on the sample being processed, the other molecules in the sample mixture, and the type of separation carried out. Preferably, the first ion-permeable barrier is a large pore sized membrane such as a polycarbonate membrane. The second and third barriers are preferably restriction membranes having a molecular mass cut off less than that of the first membrane. A restriction membrane is also preferably formed from polyacrylamide. The molecular mass cut-off of the restriction membranes will depend on the sample being processed, the other molecules in the sample mixture, and the type of separation carried out. It will be appreciated that the second ion-permeable barrier may have a different molecular mass cut off to the third ion-permeable barrier.

In another form, the second and third ion-permeable barriers are membranes having characteristic average pore size and pore-size distribution.

The present invention can result in recovery rates of at least 50% active sperm type of choice. The recovery rates can be much higher and in the order of about 60% or greater. Preferably, recovery rates are at least about 70%, more preferably at least about 80%, even more preferably at least about 90%, or up to about 95% of the at least one sperm type remains viable or substantially unchanged after separation.

The sample may be processed in a static form in batches or may be processed by moving the sample and electrolyte in streams through the apparatus. By convenience, the first sample chamber is called stream 1 and the second sample chamber is called stream 2.

It will be appreciated that voltage, field strength and electrophoresis run times can vary depending on the sperm type, apparatus and medium used. It is within the skill of the operator to determine optimum conditions for a given cell separation run.

Preferred buffer concentrations are between about 1 to 100 mM. Any suitable buffer or electrolyte can be used. Suitable buffers include, but not limited to, sperm-compatible biological buffers and components such as HEPPS, HEPES, BisTris, sodium chloride, phosphate buffer salts, sucrose, glucose and mannitol. In experiments outlined below, a 10 mM buffer of HEPES, 30 mM NaCl and 0.2 M sucrose has been found to be particularly useful. It will be appreciated, however, that any other suitable buffer can be used.

In a second aspect, the present invention provides use of a sperm type separated by the process according to the first aspect of the present invention to fertilize an ovum.

In a third aspect, the present invention provides use of a membrane-based electrophoresis apparatus to separate a sperm type from a sperm population.

In a fourth aspect, the present invention provides a sperm type obtained by the process according to the first aspect of the present invention.

The process according to the present invention is suitable for separating sperm from animals including humans. The separated sperm can be used for artificial insemination (AI) or in vitro fertilisation (IVF) applications. The separated sperm can be stored by freezing for example, or used fresh, depending on the application.

Gradiflow™ and Microflow™ are trademarks owned by Gradipore Limited, Australia.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the present invention may be more clearly understood, preferred forms will be described with reference to the following drawings and examples.

BRIEF DESCRIPTION OF THE DRAWINGS

FIG. 1 shows percentage of normal spermatozoa in electrophoretic fractions. Percentage of normal spermatozoa resulting from morphological assessment of separated and excluded populations using the Papanicolaou staining method (Menkveld R., Stander, F. S. H., Kotse, T. J. vW., Kruger, T. F., Van Zyl, J. A. (1990) The evaluation of morphological characteristics of human spermatozoa according to strict criteria. *Hum Reprod.* 5:586-592) demonstrated a significantly greater proportion of normal sperm with the separated fraction ($P<0.001$). Data expressed as mean±SEM (n=4) for separated and excluded populations for each respective electrophoretic time-point undertaken. Note: Time zero denotes sperm retrieved from cartridge after 300 s incubation, with no application of electrophoretic treatment.

FIG. 3 shows TUNEL analysis for DNA damage in electrophoresed and fractionated spermatozoa populations. Percentage TUNEL-positive cells for separated and excluded sperm populations for 0-15 min time-points show a significantly reduced presence of detectable DNA damage for all separated sperm populations, as compared to the results for excluded populations (P<0.001). Represented is the mean (n=6) values±SEM for separated and excluded sperm populations. Positive controls (1 mg/ml DNAse) indicated efficient labelling of dsDNA lesions and negative controls (no TdT enzyme) assured no non-specific labelling of cells.

MODE(S) FOR CARRYING OUT THE INVENTION

Before describing the preferred embodiments in detail, the principal of operation of a membrane-based electrophoresis apparatus will first be described. An electric field or potential applied to ions in solution will cause the ions to move toward one of the electrodes. If the ion has a positive charge, it will move toward the negative electrode (cathode). Conversely, a negatively-charged ion will move toward the positive electrode (anode).

In the apparatus used for present invention, ion-permeable barriers that substantially prevent convective mixing between the adjacent chambers of the apparatus or unit are placed in an electric field and a cell type or population in the sample is selectively transported through an ion-permeable barrier. The particular ion-permeable barriers used will vary for different applications and generally have characteristic average pore sizes and pore size distributions and/or isoelectric points allowing or substantially preventing passage of different components.

Apparatus

A number of membrane-based electrophoresis apparatus have been developed by, or in association with, Gradipore Limited, Australia. The apparatus are marketed and used under the name Gradiflow™. In summary, the apparatus typically includes a separation cartridge or zone which houses a number of membranes forming at least two chambers, cathode and anode in respective electrode chambers connected to a suitable power supply, reservoirs for samples, buffers and electrolytes, pumps for passing samples, buffers and electrolytes, and cooling means to maintain samples, buffers and electrolytes at a required temperature during electrophoresis. The cartridge or zone contains at least three substantially planar membranes disposed and spaced relative to each other to form two chambers through which sample or solvent can be passed. A separation membrane is disposed between two outer membranes (termed restriction membranes as their molecular mass cut-offs are usually smaller than the cut-off of the separation membrane). When the cartridge (if used) is installed in the apparatus, the restriction membranes are located adjacent to an electrode. The cartridge is described in AU 738361. Description of membrane-based electrophoresis can be found in U.S. Pat. No. 5,039,386 and U.S. Pat. No. 5,650,055 in the name of Gradipore Limited, incorporated herein by reference. An apparatus particularly suitable for use in isoelectric separation applications can be found in WO 02/24314 in the name of The Texas A&M University System and Gradipore Limited, incorporated herein by reference.

One electrophoresis apparatus suitable for use in the present invention comprises:

(a) a first electrolyte chamber;
(b) a second electrolyte chamber,
(c) a first sample chamber disposed between the first electrolyte chamber and the second electrolyte chamber;
(d) a second sample chamber disposed adjacent to the first sample chamber and disposed between the first electrolyte chamber and the second electrolyte chamber;
(e) a first ion-permeable barrier disposed between the first sample chamber and the second sample chamber;
(f) a second ion-permeable barrier disposed between the first electrolyte chamber and the first sample chamber;
(g) a third ion-permeable barrier disposed between the second sample chamber and the second electrolyte chamber; and
(h) electrodes disposed in the first and second electrolyte chambers.

The electrophoresis apparatus may further comprise one or more of:

(i) an electrolyte reservoir;
(j) a first sample reservoir and a second sample reservoir;
(k) means for supplying electrolyte from the electrolyte reservoir to the first and second electrolyte chambers; and (l) means for supplying sample or liquid from at least the first sample reservoir to the first sample chamber, or from the second sample reservoir to the second sample chamber.

The apparatus may comprise:

(m) a first electrolyte reservoir and a second electrolyte reservoir; and (n) means for supplying electrolyte from the first electrolyte reservoir to the first electrolyte chamber and electrolyte from second electrolyte reservoir to the second electrolyte chamber.

The apparatus may further comprise one or more of:

means for circulating electrolyte from the electrolyte reservoir(s) through the electrolyte chambers forming electrolyte streams in the electrolyte chambers; and means for circulating contents from each of the first and second sample reservoirs through the respective first and second sample chambers forming first and second sample streams in the respective sample chambers;

means for removing and replacing sample in the first or second sample reservoirs; and means to maintain temperature of electrolyte and sample solutions.

The ion-permeable barriers typically prevent substantial convective mixing of contents of the adjacent chambers.

In one form, the first ion-permeable barrier is a membrane having a characteristic average pore size and pore size distribution. In one preferred form, all the ion-permeable barriers are membranes having a characteristic average pore size and pore size distribution. This configuration of the apparatus is suitable for separating compounds on the basis of charge and or size.

In another form, the second and third ion-permeable barriers are membranes having a characteristic average pore size and pore-size distribution.

In order to control substantial bulk movement of liquid under the influence of an electric field an inducible electro-endo-osmotic membrane can be used in at least one of the second or third ion-permeable barriers. The inducible electro-endo-osmotic membrane is preferably a cellulose tri-acetate (CTA) membrane. It will be appreciated that the inducible electro-endo-osmotic membrane can be formed from any other suitable membrane material such as poly(vinyl alcohol) cross-linked with glutaraldehyde (PVAl+glut).

The present inventors have found that a polycarbonate membrane having a pore size of about 5 µm is particularly suitable for use in the apparatus. It will be appreciated that other molecular mass cut-offs would also be suitable for the apparatus. The pore size should be sufficiently large for sperm to pass.

The electrophoresis apparatus may contain a separation unit housing the chambers and ion-permeable barriers which is provided as a cartridge or cassette fluidly connected to the electrolyte reservoir(s) and, if present, the sample reservoirs.

In use, a sample containing cells to be separated is placed in the first or second sample chamber. Electrolyte is placed in the first and second electrolyte chambers. Electrolyte or other liquid can be placed in the first and/or second sample chamber. An electric potential is applied to the electrodes wherein a cell type in the first and/or second sample chamber is caused to move through a diffusion barrier to the second and/or first sample chamber.

Methods

An example of an application for the present invention has been in the area of human semen fractionation. A method has been developed for separating semen populations into fractions enriched for healthy sperm using a bench top analytical-scale apparatus, termed the Microflow™ apparatus by Gradipore Limited. This apparatus was originally developed to separate macromolecules in small volumes and is described in WO 01/78878, incorporated herein by reference.

Sperm Samples

Semen samples were obtained by masturbation through an internal donor program, with a minimum of three days abstinence. All samples were liquefied at RT for 30 min and subjected to routine semen analysis performed according to the WHO guidelines (WHO, 1999). All investigations involving the use of human materials were approved by the University of Newcastle Human Ethics Committee.

Electrophoresis Separation Conditions

Buffer: 10 mM HEPES, 30 mM NaCl, 0.2 M sucrose, pH 7.4
Buffer osmolarity: 310 mOsmol $kg^{-1}$
Temperature: 23° C.
Conductivity: 4 mS/cm
Separation Membrane: 5 or 10 µm polycarbonate
Restriction Membrane: 10 kDa polyacrylamide
Applied current: 75 mA
Time: 0, 30, 60, 90, 120, 300, 600, 900 seconds
Electric field strength: 16-18 V/cm Sperm Vitality Human sperm samples were assessed for vitality using eosin dye exclusion test. This test relies on the fact that intact and functional plasma membranes of live cells are able to exclude extracellular substances, however, dead cells have non-functional or damaged plasma membranes, and subsequently cannot exclude the dye. Ten µl of a 0.05% eosin dye solution in PBS was mixed with 10 µl of sample containing sperm population on a slide. On examination under phase contrast at 400× magnification, the cytoplasm of live cells appeared clear in colour, whereas that of dead cells appeared to be coloured pink or red. 200 cells were scored for each sample, and results were recorded as a percentage of live cells.

Sperm and Round Cell Density Counts

The concentrations of relevant sperm populations were calculated by making a 1:20 dilution with sperm dilution fluid containing formalin to render the sperm immotile, and 10 µl was placed into one chamber of an improved Neubauer haemocytometer. Samples were then allowed to settle by placing the haemocytometer inside a humid covered Petri dish for 5 minutes. All 25 large squares of the haemocytometer were counted and the resulting number was divided by the conversion factor of 5 to determine the concentration of sperm, in millions of cells/ml.

Sperm Motility

Sperm were wet-mounted and assessed for motility using phase contrast microscopy. Slides were scored immediately after preparation, with any directional movement of cells being classed as motile in contrast to totally immotile sperm. At least 100 cells were scored at 200× magnification, and motilities were recorded as percentage motile sperm.

Computer Assisted Sperm Assessment (CASA)

A 10 µl sample of spermatozoa was aliquoted onto a pre-warmed disposable slide of fixed chamber depth 30 µm. Motion parameters were then captured using a 240V B/W CCD Camera (Panasonic, Belrose, NSW) at a frame rate of 50 Hz and contemporaneously recorded using dark-field illumination on professional-grade Super VHS videotape and Super VHS videotape recorder (JVC, Kingsgrove, NSW). Samples were evaluated with the Hamilton-Thorn semen analyzer (CASA, HTM-IVOS), as previously outlined for human sperm (Olds-Clarke, P., Baer, H. M., Gerber, W. L. (1990) Human sperm motion analysis by automatic (Hamilton-Thorn Motility Analyzer) and manual (Image-80) digitization systems. *J Androl.* 11 (1):52-8).

TUNEL (Terminal Deoxynucleotidyl Transferase (TdT)-Mediated dUTP Nick-End Labelling)

Fractionated sperm cells for each electrophoretic timepoint were fixed in 4% para-formaldehyde in PBS at 4° C. for >15 min. Cells were then washed twice in filtered PBS and resuspended in PBS to an appropriate concentration for consistent smear preparation. Treatments were smeared onto pre-prepared poly-l-lysine coated slides and allowed to dry at RT. Dried smears were then assayed using TUNEL methodology or stored at −20° C. for future analysis.

Smeared slides were permeabilised for 2 min at 4° C. using 0.1% Triton X-100 in 0.1% sodium citrate, then digested using Proteinase K (100 μg/ml) for 15 min at 37° C. Relevant wells for assay positive controls were then treated with DNAse (1 mg/ml in PBS) for 10 min at 37° C., all other wells overlayed with 1×TE buffer. Finally, smears were blocked with 1% BSA in PBS for 15 min at RT, prior to the application of TUNEL reaction components.

TUNEL assay was performed using the in situ cell death detection kit (Fluorescein) from Boehringer Mannheim (Mannheim, Germany). Reagents were diluted in 1×PBS as the use of undiluted reagents in our experience created high levels of background and non-specific staining which hampered the analysis for TUNEL positive cells. Un-diluted terminal deoxynucleotidyl transferase (TdT) from calf thymus (EC 2.7.7.31) in storage buffer (25 μl) was mixed with label solution (nucleotide mixture in reaction buffer) diluted 1:5 with PBS (225 μl) to provide 250 μl of TUNEL reaction mixture. A negative control consisting of nucleotide solution without TdT enzyme was included in all experiments. Ten μl of relevant TUNEL treatment mix was added to the spermatozoa in each well and slides were incubated for 1 hr at 37° C. in a humid chamber depriving the slides of light and preventing evaporative loss. Slides were then washed in PBS and mounted in Mowiol (2.4 g Mowoil (Calbiochem, La Jolla, Calif.), 6 g glycerol, 6 ml dH20, 12 ml 0.2M Tris (pH 8.5), 2.5% 1,4-diazobicyclo-{2.2.2}-octane (DABCO)), and viewed using a Ziess Axioplan2 fluorescence microscope with selective filters for FITC fluorescence.

Sperm Morphology

Fractionated sperm cells for each electrophoretic timepoint were diluted in PBS to appropriate concentration for consistent smear preparation. Treatments were smeared onto pre-prepared poly-l-lysine coated slides and allowed to dry at RT. Dried smears were fixed in 95% ethanol for 15 min at RT then stained by a modification of the Papanicolaou method, as described by Belsey et al 1980 (Belsey, M. A., Eliasson, R., Gallegos, A. J., Moghissi, K. S., Paulsen, C. A., Prasad, M. R. N. 1980) Laboratory Manual for the Examination of Human Semen and Semen-Cervical Mucus Interactions. Press concern, Singapore) or stored at −20° C. for future analysis.

Spermatozoa smears were rehydrated for 3 min in 50% ethanol, rinsed for 10 s in $dH_2O$ and stained with Harris' haematoxylin for 3 min. Smears were then washed twice with running tap $H_2O$ for 5 min, separated by acid ethanol (0.25% HCl in 70% EtOH) treatment for 2 s. Following a brief 1 s dip in $dH_2O$ smears were progressively dehydrated in 50, 70, 80, 95% EtOH for 10 s then incubated with Orange G6 cytoplasmic stain for 2 min. Surplus stain was removed by 95% EtOH for 20 s and EA-50 cytoplasmic and nucleolar staining performed for 5 min. Smears were then dehydrated (95% EtOH 15 s, 100% EtOH 2 min), allowed to completely air-dry and mounted using DPX media.

Smears were viewed using a Zeiss Axioplan 2 microscope under bright field illumination employing a 100× oil-immersion objective and a total magnification of 1250×.

The classification and evaluation of sperm morphology, along with the normal criteria for whole spermatozoa, was established according to Menkveld et al., 1990. The entire spermatozoon (head, neck, midpiece and tail) was taken into consideration for evaluation along with any germinal epithelium or other cell types present. Spermatozoa were classified into one of seven groups, normal (whole sperm), large, small, elongated, duplicated and amorphous heads, all with or without the presence of a cytoplasmic droplet and/or tail, neck and/or midpiece defect (Menkveld et al., 1990). The seventh group consisted spermatozoa with a normal head with a tail and/or a neck and/or a midpiece defect and/or the presence of a cytoplasmic droplet (Menkveld et al., 1990). Tail, neck and midpiece defects, loose heads, germinal epithelium and unknown cells were recorded separately and expressed per 100 spermatozoa (Menkveld et al., 1990). A minimum of 100 spermatozoa were analysed with the aid of an eyepiece micrometer.

Acrosome Reactions (*Arachis hypogaea* Stain) & HOS Vitality Assessment

Subsequent to electrophoretic treatment, samples where incubated in BWW at 37° C. in the presence of 5% $CO_2$ in air for a minimum of 3 hr to capacitate the cells. Sperm were then treated with the calcium ionophore A23187 for 30 min at a final working concentration of 2.5 μM to induce acrosome reactions. An equivalent dilution of DMSO was used as a vehicle control for each sperm population. Samples were then subjected to HOS vitality tests prior to staining for the acrosome reaction. These were first centrifuged at 1000×g to remove treatment media, resuspended in HOS, and incubated for 1 hr at 37° C. These samples were then centrifuged at 1000×g for 5 minutes to remove the media.

Sperm were fixed in 4% para-formaldehyde for 5 min at 4° C., centrifuged at 2000×g for 1 min, pellets were resuspended in filtered PBS and centrifuged again, and pellets were permeabilised by resuspending in 0.2% Triton X-100 for 10 min. Samples were then, centrifuged at 1000×g for 1 min, and pellets were resuspended in PBS. Five μl of each sample was spotted onto the wells of a diagnostic slide and allowed to air dry. Samples were stained with fluorescein isothiocyanate (FITC)-conjugated *A. hypogaea* lectin (1 mg/ml of PBS) for 15 minutes in the dark at 4° C. Slides were washed with PBS, mounted in Mowiol, and visualised by fluorescence microscopy. At least 100 cells were scored for each sample, and results were expressed as percentage of live acrosome-reacted spermatozoa.

Statistical Analysis

Each experiment was repeated 3-6 times and statistical analysis was performed using Microsoft Excel® 2000 and SuperANOVA (Abacus Concepts Inc, CA, USA). Angular transformations were carried out for percentages prior to statistical analysis using an angular transformation table, where $p=\sin^2$. Averages were calculated for each experiment, as well as standard errors of the mean (SEM) for n−1. Post-hoc testing was performed using Fischer's Protected Least Significant Difference (PLSD). Samples with a P-value of <0.05 were considered significant.

Results

The results demonstrated the selective capacity of this approach to separate functional spermatozoa from the contaminating constituents of human semen. The cell separation system isolated a highly purified subpopulation of spermatozoa characterized by significantly better morphology, improved vitality, motility and enhanced functional competence, compared with the excluded population. In addition, the selected population of spermatozoa exhibited significantly lower levels of DNA damage than their unselected counterparts. Moreover, this selection process was achieved in a fraction of the time taken to purify human spermatozoa using alternative selection procedures such the Percoll gradient centrifugation or 'swim-up' methods.

Figure 1:
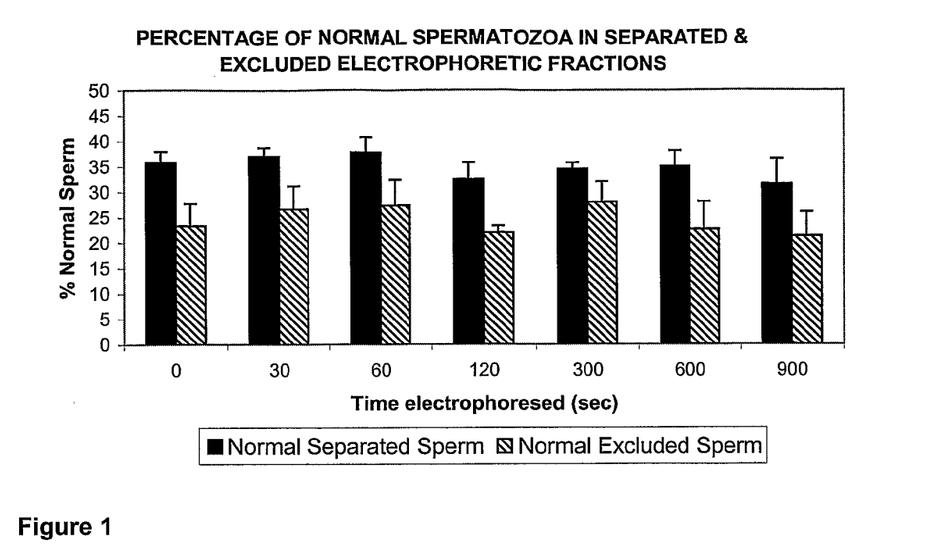
Figure 2:
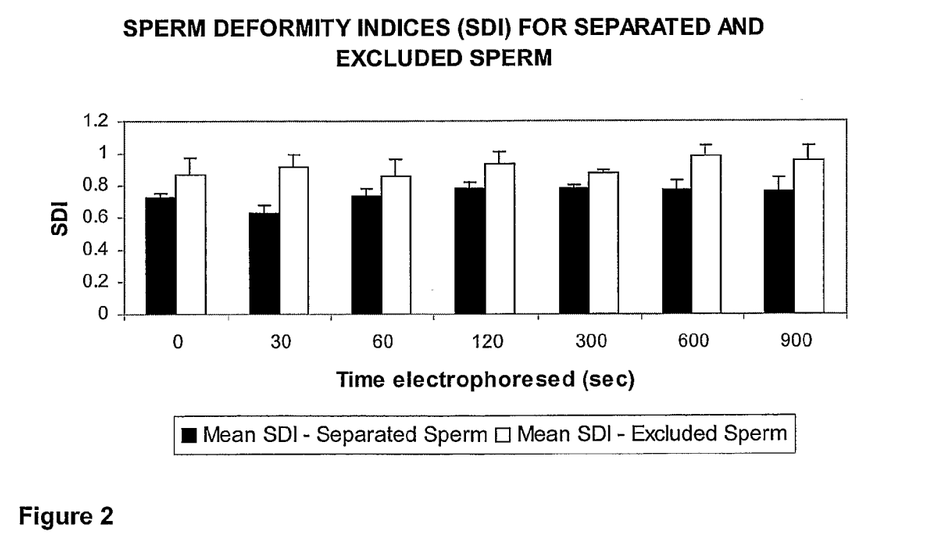
FIG. 2 shows sperm deformity indexes for populations of spermatozoa in electrophoretic fractions. Morphological assessment of separated and excluded sperm populations using the sperm deformity index (SDI). Shown are the mean (n=4) SDI values±SEM for separated and excluded sperm populations. Results indicate significantly less morphological defects for all separated populations (P<0.001) and no significant effect of treatment time.

In terms of the morphology of the cells, the data presented in FIG. 1 indicated a statistically significant higher proportion of spermatozoa with normal morphology in the separated fraction (35±1.2%) compared to that of the excluded fraction (28±4%) after 5 min treatment (P<0.001). This result was observed for all electrophoretic time points assessed (FIG. 1), and for all samples analysed irrespective of the level of morphological heterogeneity in the starting cell population.

The results were obtained using standard morphological assessment criteria established by the World Health Organization 1999 (World Health Organization. WHO laboratory manual for the examination of human semen and sperm-cervical mucus interaction (4th edn. ed.), Cambridge University Press, Cambridge 1992). These data were reinforced when the morphology was assessed using an alternative assessment technique, the sperm deformity index (SDI) introduced by Panidis et al. 1998 (Panidis, D., Matalliotakis, I., Papathanasiou, K., Roussos, C., Koumantakis, E. (1998) The sperm deformity and the multiple anomalies indexes in patients who underwent unilateral orchectomy and preventative radiotherapy. *Euro J Ob & Gyn & Repro Bio.* 80:247-250). This criterion has been shown to provide a correlation between the morphology status of a given sperm population and its potential for fertilisation in vitro. In this study, the SDI values recorded for the separated sperm populations was significantly below the threshold SDI value of 0.93 (Panidis et al. 1998) for all electrophoretic time-points. As SDI values increase above this threshold, the fertilising capacity of the sperm proportionally decreases. Conversely, a progressive improvement in fertility outcomes is observed as values decrease from this point (Panidis et al. 1998). This selection of a sub-population of morphologically normal spermatozoa, with low SDI values demonstrates enrichment for this important correlate of fertilisation.

Figure 3:
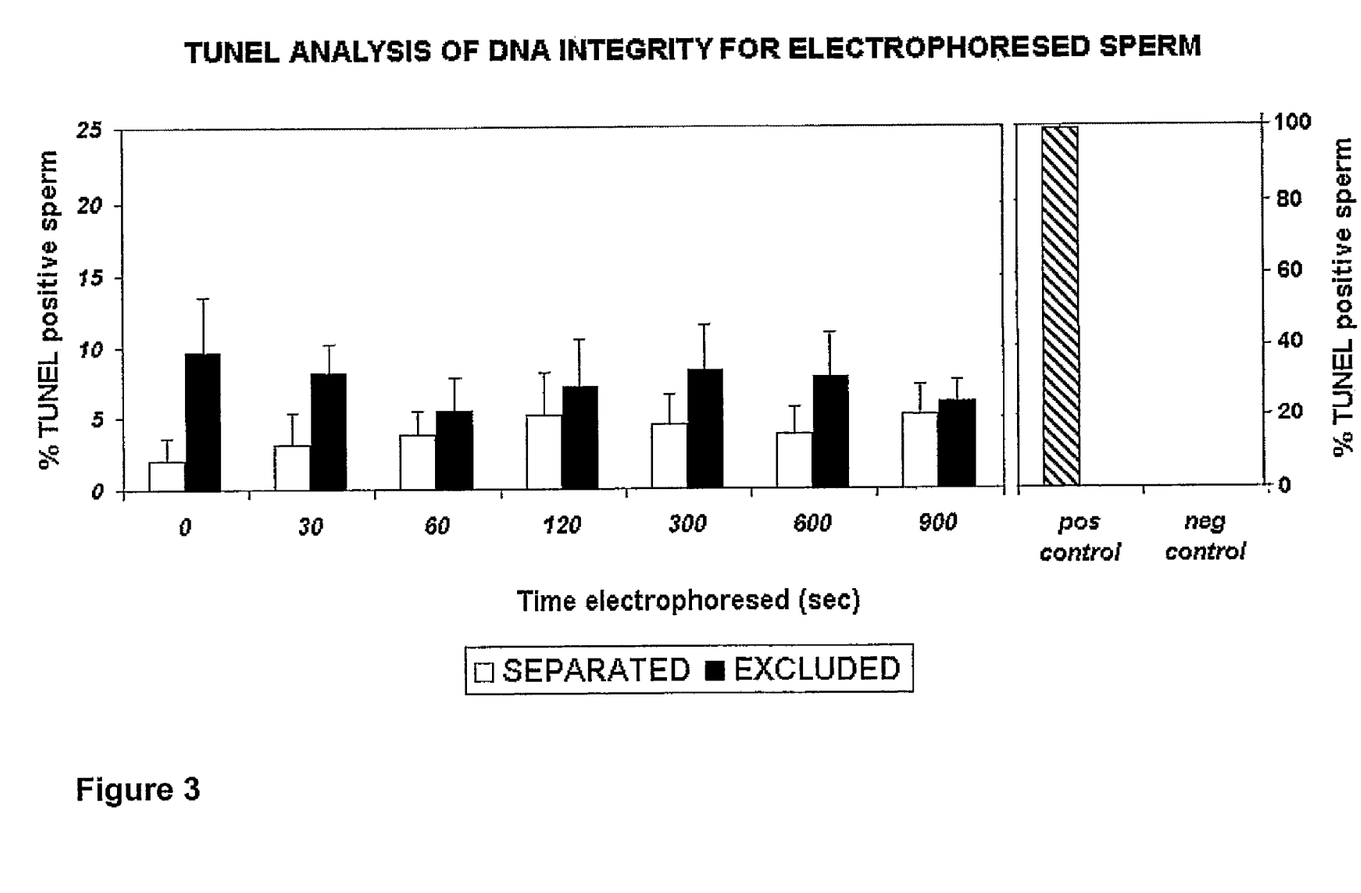

The separated populations of spermatozoa also expressed lower levels of detectable DNA damage (4.5±2%) as compared to the excluded populations (8.3±3.6%) after 5 min electrophoresis. The TUNEL assay revealed a significant difference (P<0.001) in labelled cells between separated and excluded sperm populations, however, there was no significant increase in TUNEL-labelled cells with time. The percentages of detected DNA damage for separated and excluded fractions are shown in FIG. 3, which demonstrates significantly (p<0.001) lower levels of DNA damage for all separated populations and no significant effect of time on either separated or excluded time-dependent populations.

Figure 4:
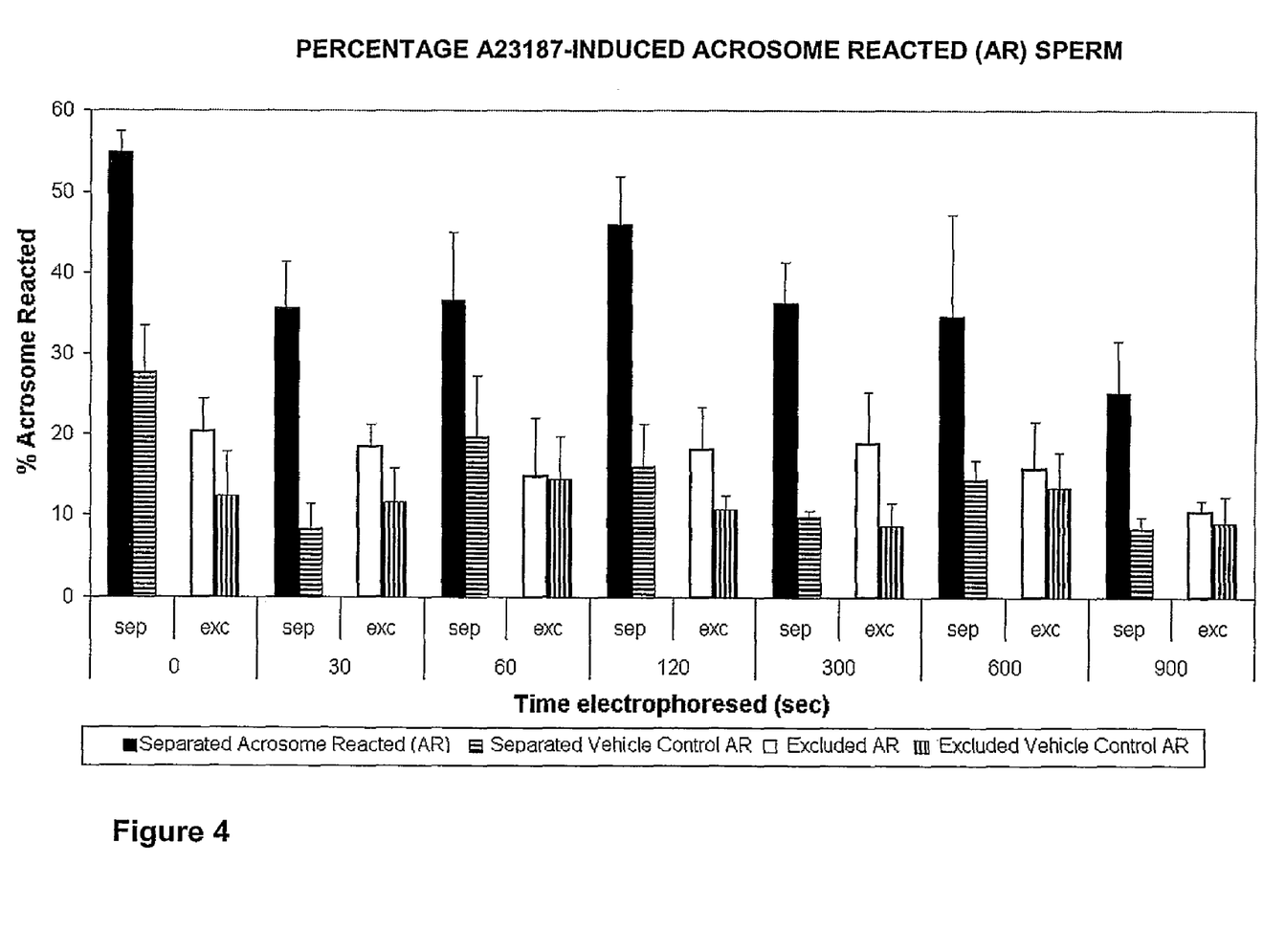
FIG. 4 shows percentage A23187-induced acrosome reacted sperm for electrophoretic fractions. Percentage A23187-induced acrosome reacted (AR) sperm and vehicle control (DMSO)-induced acrosome reacted sperm for separated (sep) and excluded (exc) sperm populations. A significant difference between separated and excluded populations can be observed for all time-points (P<0.001), and shown is the mean (n=3)±SEM for electrophoretic time-points 0-15 min. DMSO-induced AR was used to gauge non-physiological AR.

Furthermore, subsequent to the proposed treatment regime, separated populations retained a greater capacity for acrosomal exocytosis (36.3±5%) compared to excluded populations (18.7±7%) after a 5 min electrophoretic treatment. A significantly greater proportion of the separated sperm populations displayed the ability to undergo this secretory process (a pre-requisite of fertilization) as compared to the excluded population (FIG. 4; P<0.001). The results also indicated that the time of electrophoresis did not impact significantly upon the ability of these cells to acrosome react up to the 600 sec treatment time-point, however 900 s treatment appears to reduce the ability of these to undergo the acrosome reaction.

Figure 5:
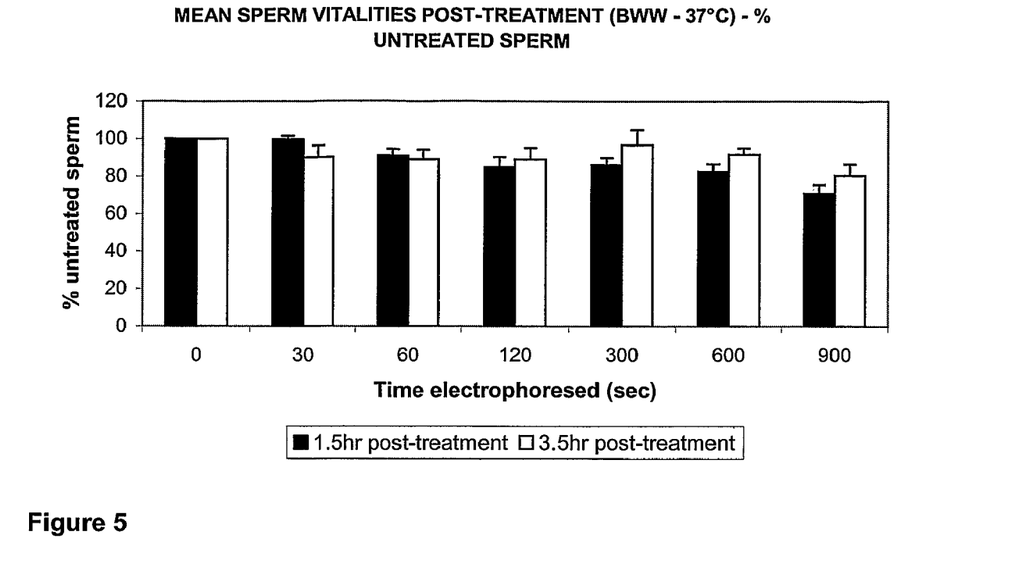
FIG. 5 shows the mean sperm vitalities of separated fractions of spermatozoa subsequent to post-treatment incubation/s. Vitalities of separated sperm populations expressed as percentage of untreated sperm (T=0), for sperm incubated in BWW at 37° C. for 1.5 hr and 3.5 hr post-treatment. Shown are the mean (n=6)±SEM of percent viable sperm.
Figure 6:
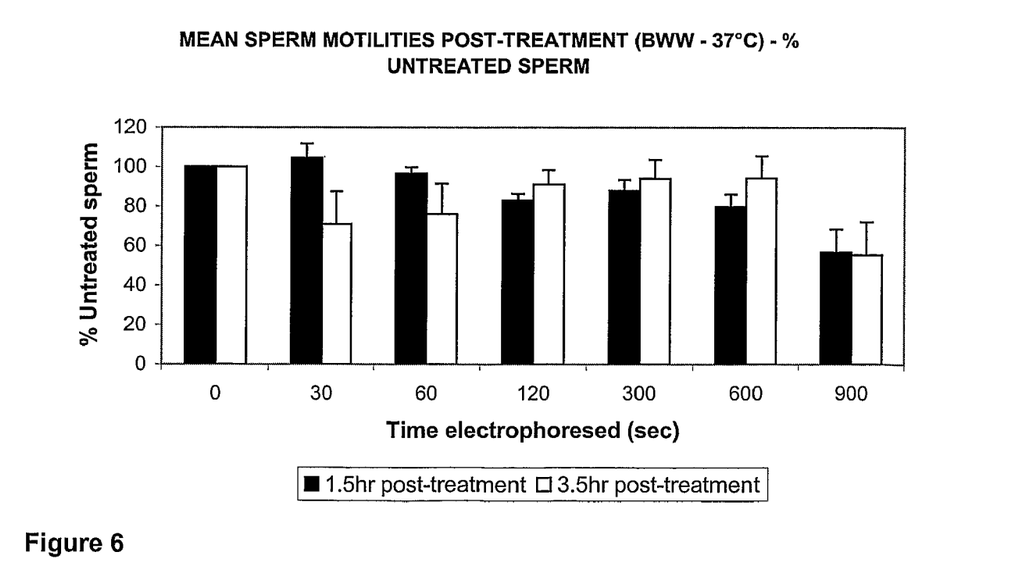
FIG. 6 shows the mean sperm motilities of separated fractions of spermatozoa subsequent to post-treatment incubation/s. Motilities of separated sperm populations expressed as percentage of untreated sperm (T=0), for sperm populations incubated in BWW at 37° C. for 1.5 hr and 3.5 hr post-treatment. Shown are the mean (n=6)±SEM percent motilities with a minimum of 100 cells counted.

Sperm vitality studies were also performed to provide a comparative indication of the 'health' of treated (separated and excluded) and untreated sperm. The eosin-exclusion test, which results in the staining of non-viable sperm, was used and the results for the percentage of viable cells before and after treatment for separated and excluded fractions are shown in FIG. 5. Five minute electrophoretic separations resulted in a mean sperm vitality of 77±5% 1.5 hr after separation. These data showed a relatively small difference in vitality compared to untreated populations (89±3%). Furthermore 3.5 hr post-treatment, sperm vitality had recovered to 80±5% showing no appreciable loss of vitality (84±5%) compared to untreated populations. Thus these results, expressed as percentage of untreated sperm, show an enrichment of viable spermatozoa and the maintenance of this vitality with no appreciable loss over time (up to 3.5 hr post-treatment).

The motility of spermatozoa from all electrophoretic time-points was also assessed to evaluate differences between separated and excluded populations and potential effects of the treatment regime employed. Five minute electrophoretic separations resulted in a mean sperm motility of 68±6% 1.5 hr after separation. This data showed a relatively small difference in motility (78±5%) compared to untreated populations. Furthermore 3.5 hr post-treatment, sperm motility had recovered to 70±5%, which was 94±10% of the value recorded in the untreated sperm populations.

Figure 7:
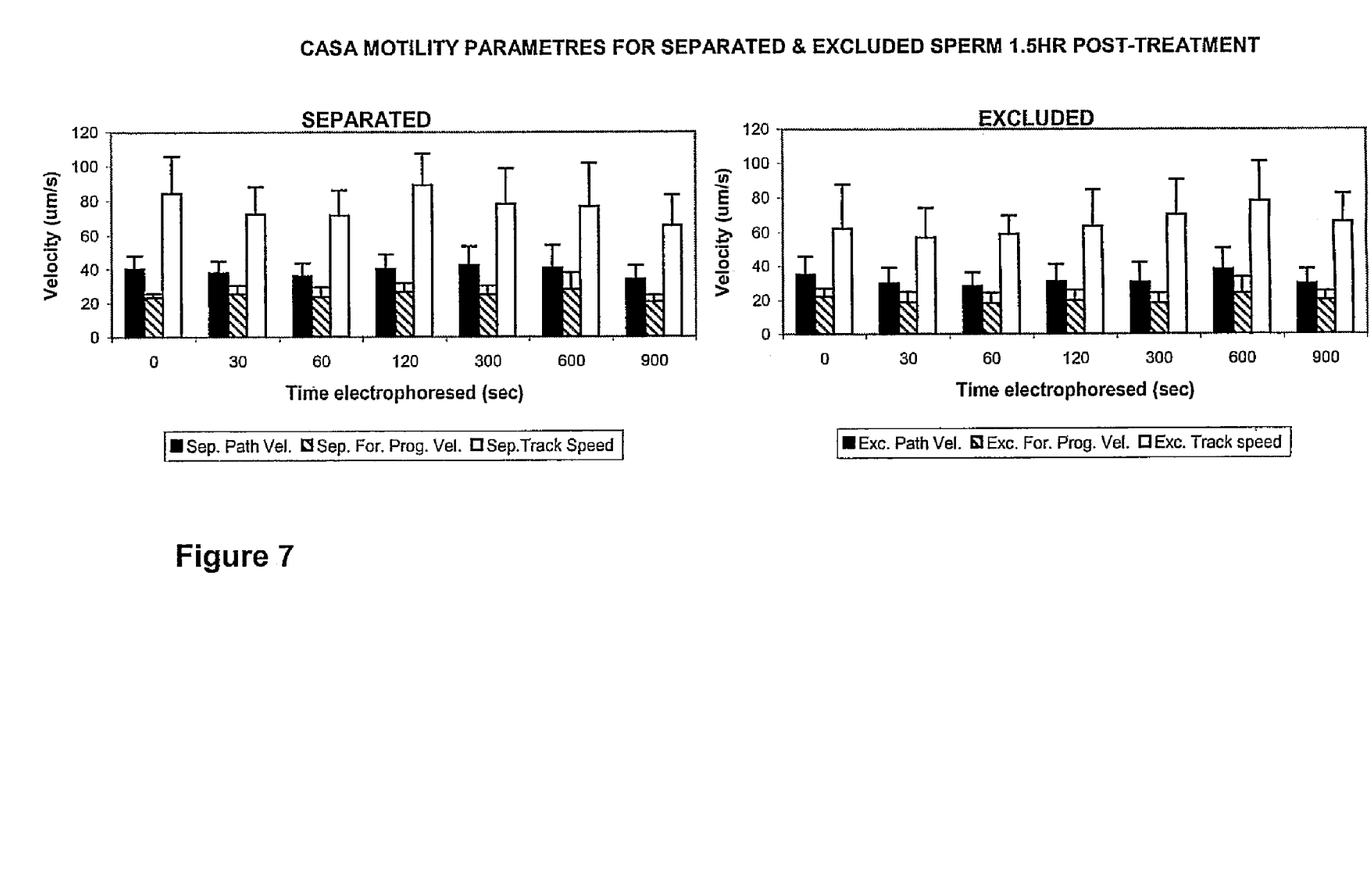
FIG. 7 shows computer assisted sperm assessment (CASA) analysis of sperm path velocity, forward progressive velocity and track speed parameters of separated and excluded fractions of spermatozoa subsequent to 1.5 hr post-treatment incubation. CASA analysis of sperm path velocity, forward progressive velocity and track speed for separated (Sep) and excluded (Exc) populations at all electrophoretic time-points. Analysis performed subsequent to 1.5 hr incubation in BWW at 37° C., with a minimum, of 100 cells analysed. Shown is the mean (n=3)±SEM.

Not only were the percentage motility values unchanged by exposure to the electrophoretic conditions employed in this study, but also Computer Assisted Sperm Assessment (CASA) demonstrated that these populations of separated spermatozoa displayed track speeds and levels of path and forward progressive velocities that were not significantly different from those recorded in the excluded populations (FIG. 7).

Figure 8:
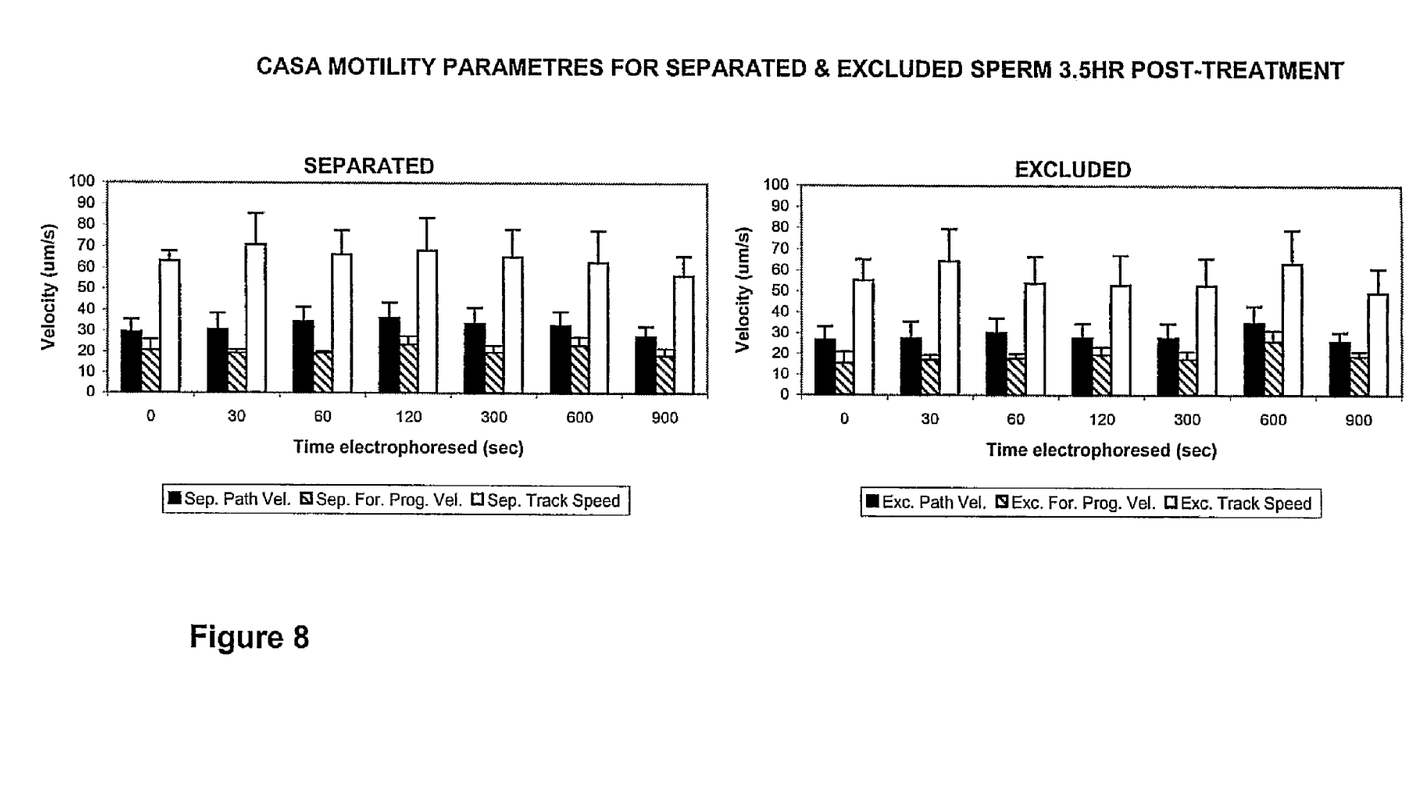
FIG. 8 shows computer assisted sperm assessment (CASA) analysis of sperm path velocity, forward progressive velocity and track speed parameters of separated and excluded fractions of spermatozoa subsequent to 3.5 hr post-treatment incubation. CASA analysis of sperm path velocity, forward progressive velocity and track speed for separated (Sep) and excluded (Exc) populations at all electrophoretic time-points. Analysis performed subsequent to 1.5 hr incubation in BWW at 37° C., with a minimum, of 100 cells analysed. Shown is the mean (n=3)±SEM.
Figure 9:
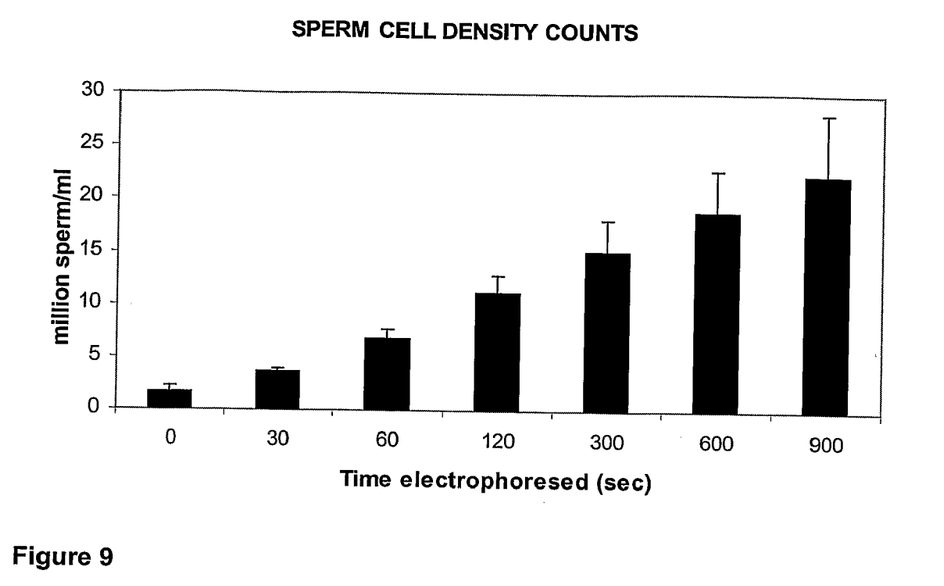
FIG. 9 shows sperm cell density counts for separated fractions resulting from time-dependent treatments.

FIG. 8 shows the CASA motility parameters for separated and excluded sperm populations 3.5 hr post-treatment, and is again characterized by acceptable motilities for both separated and excluded sperm, and no significant difference from those observed for the corresponding excluded time-points. There was no appreciable difference between the results 1.5 and 3.5 hr post treatment, which demonstrated a retained capacity for the motility parameters studied for all populations subjected to sperm cell electrophoresis.

Subsequently, CASA analysis showed no significant effect of electrophoretic treatment time or time elapsed post-treatment (up to 3.5 hr) on the motility parameters studied for either separated or excluded populations. This indicated that although separated sperm populations had a greater number of motile cells, the motion parameters of the cells in both populations cannot be discriminated in terms of their forward progressive velocities, path velocities and their track speeds.

Experiments also showed a progressive accumulation of spermatozoa in the separated fraction with increased treatment time, yielding an average of $15.13 \times 10^6 \pm 3.0 \times 10^6$ sperm/ml after 5 min treatment. For all separated time-points zero round cell contaminants were counted, their size-exclusion supporting the purification properties of this treatment regime, in terms of its ability to separate healthy spermatozoa from contaminating constituents of semen.

Clinical Work

One of the key attributes of the gamete separation system is that it can isolate spermatozoa exhibiting low levels of DNA damage. Since DNA damage in spermatozoa is clinically correlated with poor fertility, low rates of fertilization, impaired embryonic development, abortion and childhood disease, this facility should be of value in treating infertile couples whose pathological profile is dominated by DNA damage in the male germ line.

In light of these considerations a couple was selected, characterized by long term infertility in association with high levels of DNA damage in the spermatozoa. Using the electrophoretic gamete separation procedure, a subpopulation of sperm was successfully isolated from the male partner exhibiting reduced levels of DNA damage. These cells were subsequently used for assisted conception therapy by Sydney IVF and a pregnancy successfully induced.

This is the first example of a human pregnancy being created using electrophoretically separated spermatozoa and the successful outcome demonstrates the clinical potential of this approach in the treatment of infertility patients.

SUMMARY

Parameters Investigated
    Sperm motility—manual counts & CASA
    Sperm vitality—eosin exclusion test
    Sperm & round cell density—manual counts
    DNA integrity—TUNEL assay
    Sperm morphology—Papanicolaou staining
    Functional competence—A23187-induced acrosome reaction Demonstrated Results Enrichment of viable/motile sperm that show no appreciable loss of vitality or motility over experimental time frame (up to 3.5 hr) or as a result of time electrophoresed;

Separated fractions showed a greater percentage of sperm with normal morphology and a better sperm deformity index (SDI) for all time-dependant populations, indicating a higher probability of fertility outcomes for these populations;

Separated fractions showed an enhanced ability to undergo induced acrosome reactions indicating the fertilizing capacity of these cells was greater than that of excluded populations;

Separated fractions showed lower levels of DNA fragmentation for all time-dependant populations and TUNEL analysis also showed no significant difference in DNA damage with treatment time indicating no induction of DNA fragmentation as a result of the treatment regime employed; and ~$15 \times 10^6$ sperm/ml fractionated in 5 min, with zero round cell contamination of separated sperm populations.

The present invention uses a membrane-based electrophoresis system based on the Gradiflow™ technology developed by Gradipore Limited, designed to enrich for, or remove, a cell population(s) from a cell suspension mixture of cell types. The technology incorporates a disposable membrane cartridge consisting of at least two membranes housed within the separation unit of the instrument. An arrangement of $\geq 1$ separation membrane(s) between 2 restriction membranes forms (n+1) chambers, where n is the number of separation membranes inserted. Electrophoresis buffer is positioned or circulates on the outside of the restriction membranes and performs the dual function of setting the pH of the system and cooling the electrophoresis chamber. Application of an electric potential induces migration of the cells within the separation unit. By selecting an appropriate separation membrane pore size, isolation of cells by size fractionation can be achieved.

The present invention details the first membrane-based electrophoretic system applied to the separation/enrichment of sperm population(s) from semen containing at variety of sperm types. Unlike traditional electrophoresis devices in which separation is based on relative electrophoretic mobilities of different cell types, the present membrane-based electrophoresis technology can separate sperm based on the combination of size and electrophoretic mobility. Advantages associated with the present invention for sperm separation are that it is rapid and gentle, and preserves the in vivo status of the sperm. This is in contrast to antibody-based methods which require an enzyme or chemical process to remove the affinity ligand bound to the cell surface, and thus may alter the cell surface properties.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A process for separating a sperm type from a sperm population in a sperm sample by electrophoresis comprising subjecting the sperm population to an electric potential such that a sperm type move through an ion-permeable barrier and the sperm type is separated from the sperm population through the ion-permeable barrier.

2. The process according to claim 1 wherein the sperm type has a desired characteristic selected from the group consisting of motility, robustness, gender, fertilizing potential, and combinations thereof.

3. The process according to claim 2 wherein the sperm type has fertilizing potential.

4. The process according to claim 1 wherein the sperm type has an undesired characteristic of poor motility.

5. The process according to claim 1 comprising:
providing a sample containing sperm to a sample chamber of electrophoresis apparatus comprising a first electrolyte chamber; a second electrolyte chamber; a first sample chamber disposed between the first electrolyte chamber and the second electrolyte chamber; a second sample chamber disposed adjacent to the first sample chamber; a first ion-permeable barrier disposed between the first sample chamber and the second sample chamber; a second ion-permeable barrier disposed between the first electrolyte chamber and the first sample chamber; a third ion-permeable barrier disposed between the second sample chamber and the second electrolyte chamber; and electrodes disposed in the first and second electrolyte chambers; and applying an electric potential between the electrodes causing at least one sperm type in the first or second sample chamber to move through the first ion-permeable barrier into the other of the first or second sample chamber.

6. The process according to claim 5 wherein one or more of the first, second, or third ion-permeable barriers are electrophoresis membranes having a characteristic average pore size and pore size distribution.

7. The process according to claim 6 wherein all of the ion-permeable barriers are electrophoresis membranes having a characteristic average pore size and pore size distribution.

8. The process according to claim 5 wherein the first ion-permeable barrier is a large pore sized membrane.

9. The process according to claim 8 wherein the first ion-permeable barrier is a polycarbonate membrane having a pore size of about 1 to about 10 µm.

10. The process according to claim 1 wherein the sperm sample contains at least two populations of sperm.

11. The process according to claim 1 wherein the electric potential is applied until at least one sperm type reaches a desired purity.

12. The process according to claim 1 wherein electrophoresis is carried out with a voltage range from 1 to 200 V.

13. The process according to claim 1 wherein electrophoresis is carried out with an applied current of up to about 75 mA.

14. The process according to claim 1 wherein electrophoresis is carried out with a field strength of 1 to 100 V/cm.

15. The process according to claim 14 wherein the field strength is from 16 to 20 V/cm.

16. The process according to claim 1 wherein electrophoresis is carried out from several seconds to about 15 minutes in an apparatus having a sample volume of about 100μ to about 4 ml.

17. The process according to claim 1 wherein sperm is diluted in buffer having a concentration of between 1 to 100 mM.

18. The process according to anyone of claims 1 to 17 wherein the sperm sample has a sperm concentration of between about 0.1 and $250 \times 10^6$/ml.

19. The process according to claim 18 wherein the sperm concentration is between $15 \times 10^6$/ml and $140 \times 10^6$/ml are processed.

20. The process according to claim 1 wherein at least about 50% of the sperm type remains viable or substantially unchanged after separation.

21. The process according to claim 20 wherein at least about 60% of the sperm type remains viable or substantially unchanged after separation.

22. The process according to claim 21 wherein at least about 70% of the sperm type remains viable or substantially unchanged after separation.

23. The process according to claim 22 wherein at least about 80% of the sperm type remains viable or substantially unchanged after separation.

24. The process according to claim 23 wherein at least about 90% of the sperm type remains viable or substantially unchanged after separation.

25. A method of fertilizing an ovum comprising contacting the ovum with a sperm type separated by the process of claim 1.

26. The process of claim 1, wherein 3.5 hours after treatment the separated sperm type has a motility value which is 94±10% of the motility value of untreated sperm.

27. The process according to claim 1 wherein at least about 50% of the sperm type remains substantially unchanged after separation.

28. The process according to claim 1 further comprising selecting the sperm type wherein the selected sperm type has a desired characteristic selected from the group consisting of morphological normality, low levels of DNA damage, low levels of reactive oxygen species generation, and combinations thereof.

29. The process of claim 1 further comprising selecting the sperm type wherein the selected sperm type has an undesired characteristic selected from the group consisting of poor morphology, high levels of DNA damage and high levels of reactive oxygen species generation.

* * * * *